(12) United States Patent
Wang et al.

(10) Patent No.: US 10,759,957 B2
(45) Date of Patent: Sep. 1, 2020

(54) COMPLIANT HYDROPHILIC COATINGS FOR MEDICAL DEVICES

(71) Applicant: Covidien LP, Mansfield, MA (US)

(72) Inventors: Edwin Wang, Tustin, CA (US); Edwin Bon, Lake Elsinore, CA (US)

(73) Assignee: COVIDIEN LP, Mansfield, MA (US)

( * ) Notice: Subject to any disclaimer, the term of this patent is extended or adjusted under 35 U.S.C. 154(b) by 44 days.

(21) Appl. No.: 15/712,809

(22) Filed: Sep. 22, 2017

(65) Prior Publication Data
US 2019/0092961 A1    Mar. 28, 2019

(51) Int. Cl.
| | |
|---|---|
| *A61L 29/14* | (2006.01) |
| *C09D 109/06* | (2006.01) |
| *A61L 29/08* | (2006.01) |
| *C07D 203/06* | (2006.01) |
| *C08B 37/08* | (2006.01) |
| *C08F 2/48* | (2006.01) |
| *C08K 5/3412* | (2006.01) |
| *C08L 9/06* | (2006.01) |
| *C08L 23/16* | (2006.01) |
| *C08L 33/08* | (2006.01) |
| *C08K 5/00* | (2006.01) |

(52) U.S. Cl.
CPC .......... *C09D 109/06* (2013.01); *A61L 29/085* (2013.01); *A61L 29/14* (2013.01); *C07D 203/06* (2013.01); *C08B 37/0072* (2013.01); *C08F 2/48* (2013.01); *C08K 5/3412* (2013.01); *C08L 9/06* (2013.01); *C08L 23/16* (2013.01); *C08L 33/08* (2013.01); *A61L 2420/02* (2013.01); *A61L 2420/08* (2013.01); *C08K 5/0025* (2013.01)

(58) Field of Classification Search
CPC .............................. C09D 109/06; A61L 29/14
See application file for complete search history.

(56) References Cited

U.S. PATENT DOCUMENTS

| | | | |
|---|---|---|---|
| 5,331,027 A * | 7/1994 | Whitbourne | ............ A61L 27/34 524/37 |
| 2002/0006493 A1* | 1/2002 | Chabrecek | .............. A61L 27/34 428/64.1 |
| 2009/0048537 A1* | 2/2009 | Lydon | ................... A61L 29/041 600/585 |
| 2011/0059874 A1 | 3/2011 | Rooijmans et al. | |

(Continued)

FOREIGN PATENT DOCUMENTS

| | | |
|---|---|---|
| CN | 101970583 A | 2/2011 |
| CN | 106334219 A | 1/2017 |
| EP | 0747071 A1 | 12/1996 |

OTHER PUBLICATIONS

Extended Search Report from counterpart European Application No. 18194286.3, dated Feb. 6, 2019, 8 pp.

(Continued)

*Primary Examiner* — Cachet I Proctor
(74) *Attorney, Agent, or Firm* — Shumaker & Sieffert P.A.

(57) ABSTRACT

Example compliant hydrophilic coatings including a base coat and a lubricious top coat for coating a medical device including a flexible substrate. The coatings exhibit reduced cracking and peeling in response to deformation or expansion of the flexible substrate. Example techniques for coating a medical device including a flexible substrate with compliant hydrophilic coatings.

19 Claims, 8 Drawing Sheets

(56) References Cited

U.S. PATENT DOCUMENTS

| | | | |
|---|---|---|---|
| 2012/0059317 A1* | 3/2012 | Michiyo | A61M 25/1002 604/103.07 |
| 2012/0121919 A1* | 5/2012 | Nielsen | A61L 29/085 428/520 |
| 2014/0193474 A1* | 7/2014 | Babcock | B05D 7/54 424/422 |
| 2016/0015864 A1* | 1/2016 | Yamashita | A61L 29/08 604/509 |
| 2018/0126035 A1* | 5/2018 | O'Mahony | A61L 29/085 |

OTHER PUBLICATIONS

Response to Communication pursuant to Rules 70(2) and 70a(2) and Rule 39(1) of the EPC dated Apr. 1, 2019, from couunterpart European Application No. 18194286.3, filed Sep. 25, 2019, 14 pp.
Examination Report from counterpart European Application No. 18194286.3, dated Feb. 28, 2020, 7 pp.
First Office Action and Search Report, and translation thereof, from counterpart Chinese Application No. 201811104577.1, dated Jul. 7, 2020, 15 pp.
Response to Examination Report dated Feb. 28, 2020, from counterpart European Application No. 18194286.3, filed Jul. 8, 2020, 28 pp.

* cited by examiner

COMPLIANT HYDROPHILIC COATINGS FOR MEDICAL DEVICES

TECHNICAL FIELD

This disclosure relates to coatings for medical devices, for example, compliant hydrophilic coatings.

BACKGROUND

Catheters and balloons may be used in intravascular procedures or other procedures to facilitate minimally invasive access and therapy at a target site. For example, an angioplasty catheter may include balloons mounted to the catheter that may be advanced to the target site and inflated to clear or compress a blockage, for example a stenosis. As another example, a stent delivery catheter may include a stent positioned over a balloon, which may be inflated to deploy the stent.

Surfaces of medical devices may be treated or modified to modify biological, chemical, or physical properties.

SUMMARY

Compliant hydrophilic coatings and techniques for coating medical devices including flexible substrates with compliant hydrophilic coatings are described herein. In some examples, coatings according to the disclosure may exhibit reduced or substantially no cracking, peeling, or flaking in response to deformation, flexure, or expansion of a flexible substrate coated with the coatings. Thus, deformable or expandable medical devices, for example, balloons and catheter shafts, may be provided with hydrophilic coatings that conform to surfaces of the medical devices and substantially retain integrity in response to predetermined deformations.

In some examples, an example medical device includes a flexible substrate defining a major surface, and a hydrophilic coating at least partially covering the major surface. The hydrophilic coating includes a base coat and a lubricious top coat. The base coat includes a copolymer of a thermoplastic elastomer and ethyl acrylate.

In some examples, an example technique includes applying a base coat precursor including a thermoplastic elastomer, ethyl acrylate, and a solvent on a major surface defined by a substrate of a medical device. The example technique further includes applying a top coat precursor on the base coat precursor, and curing at least one of the base coat precursor and the top coat precursor to form a hydrophilic coating. The hydrophilic coating includes a base coat at least partially covering the substrate and a lubricious top coat on the base coat.

Clause 1: A medical device comprising a flexible substrate defining a major surface; and a compliant hydrophilic coating at least partially covering the major surface, wherein the compliant hydrophilic coating comprises a base coat and a lubricious top coat, wherein the base coat comprises a copolymer of a thermoplastic elastomer and ethyl acrylate.

Clause 2: The medical device of clause 1, wherein the base coat further comprises at least one of polyethylene oxide or N-vinyl pyrrolidone, and wherein the thermoplastic elastomer comprises at least one of a styrene-isoprene thermoplastic elastomer or a polyolefin elastomer.

Clause 3: The medical device of clause 1 or 2, wherein the lubricious top coat comprises sodium hyaluronate and aziridine, or comprises a polymer selected from the group consisting of polyvinylpyrrolidone, polyethylene oxide, polypropylene oxide, polyacrylamide, methyl cellulose, polyacrylic acids, polyvinyl alcohols and combinations thereof.

Clause 4: The medical device of any of clauses 1 to 3, wherein the compliant hydrophilic coating exhibits substantially no cracking or flaking in response to an expansion of the flexible substrate to 500% of an original size of the flexible substrate.

Clause 5: The medical device of any of clauses 1 to 4, wherein the base coat is a product of thermal curing of a base coat precursor comprising a solvent, wherein the base coat precursor comprises, per 100 weight units of the solvent, about 2 weight units of ethyl acrylate, about 2 weight units of a styrene-isoprene thermoplastic elastomer, and about 1 weight unit of polyethylene oxide.

Clause 6: The medical device of any of clauses 1 to 4, wherein the base coat is a product of thermal curing of a base coat precursor comprising a solvent, wherein the base coat precursor comprises, per 100 weight units of the solvent, about 2 weight units of ethyl acrylate, about 2 weight units of a styrene-isoprene thermoplastic elastomer, about 2 weight units of a polyolefin elastomer, and about 1 weight unit of N-vinyl pyrrolidone.

Clause 7: The medical device of clause 5 or 6, wherein the lubricious top coat is a product of thermal curing of a top coat precursor comprising water, wherein the top coat precursor comprises, per 100 weight units of water, between about 0.4 and about 40 weight units of sodium hyaluronate, between about 0.02 and 0.2 weight units of aziridine, and between 0.02 and 0.1 weight units of a surfactant.

Clause 8: The medical device of any of clauses 1 to 4, wherein the base coat is a product of ultraviolet (UV) curing of a base coat precursor comprising a solvent, wherein the base coat precursor comprises, per 100 weight units of the solvent, about 1.5 weight units of ethyl acrylate, about 1.5 weight units of a polyolefin elastomer, about 1 weight unit of N-vinyl pyrrolidone, and about 0.1 weight units of a UV photoinitiator.

Clause 9: The medical device of clause 8, wherein the lubricious top coat is a product of UV curing of a top coat precursor comprising water, wherein the top coat precursor comprises, per 100 weight units of water, between about 0.2 and about 20 weight units of sodium hyaluronate, about 0.5 weight units of aziridine, about 10 weight units of polyvinyl methyl ether maleic anhydride, and between about 0.01 and about 0.05 weight units of the UV photoinitiator.

Clause 10: The medical device of any of clauses 1 to 4, wherein the base coat is a product of thermal curing of a base coat precursor comprising propylene glycol methyl ether acetate (PGMEA) as solvent, wherein the base coat precursor comprises, per 95 weight units of PGMEA, about 2 weight units of a 2% weight/volume solution of a styrene-isoprene thermoplastic elastomer ethyl acrylate in acetone, about 2 weight units of ethyl acrylate, and about 1 weight unit of 900 Dalton polyethylene oxide dissolved in methanol, and wherein the top coat is a product of thermal curing of a top coat precursor comprising water as solvent, wherein the top coat precursor comprises, per 100 weight units of water, about 2 weight units of sodium hyaluronate, about 0.05 weight units of aziridine, about 0.05 weight units of a surfactant, and about 2 weight units of 900 Dalton polyethylene oxide dissolved in methanol.

Clause 11: The medical device of any of clauses 1 to 10, wherein the medical device comprises a balloon comprising the flexible substrate.

Clause 12: The medical device of any of clauses 1 to 11, wherein the medical device comprises an elongated member comprising the flexible substrate.

Clause 13: A method comprising applying a base coat precursor comprising a thermoplastic elastomer, ethyl acrylate, and a solvent on a major surface defined by a substrate of a medical device; applying a top coat precursor on the base coat precursor; and curing the base coat precursor and the top coat precursor to form a compliant hydrophilic coating including a base coat at least partially covering the substrate and a lubricious top coat on the base coat.

Clause 14: The method of clause 13, wherein the curing comprises thermal curing at least one of the base coat precursor and the lubricious top coat precursor.

Clause 15: The method of clause 13 or 14, wherein the base coat precursor further comprises at least one of polyethylene oxide or N-vinyl pyrrolidone, and wherein the thermoplastic elastomer comprises at least one of a styrene-isoprene thermoplastic elastomer or a polyolefin elastomer.

Clause 16: The method of any of clauses 13 to 15, wherein the top coat precursor comprises sodium hyaluronate and azaridine, or comprises a polymer selected from a group consisting of polyvinylpyrrolidone, polyethylene oxide, polypropylene oxide, polyacrylamide, methyl cellulose, polyacrylic acids, polyvinyl alcohols, and combinations thereof.

Clause 17. The method of any of clauses 13 to 16, wherein curing the base coat precursor comprises thermal curing, and wherein the base coat precursor comprises a solvent, and per 100 weight units of the solvent, about 2 weight units of ethyl acrylate, about 2 weight units of a styrene-isoprene thermoplastic elastomer, and about 1 weight unit of polyethylene oxide.

Clause 18. The method of any of clauses 13 to 16, wherein curing the base coat precursor comprises thermal curing, and wherein the base coat precursor comprises a solvent, and per 100 weight units of the solvent, about 2 weight units of ethyl acrylate, about 2 weight units of a styrene-isoprene thermoplastic elastomer, about 2 weight units of a polyolefin elastomer, and about 1 weight unit of N-vinyl pyrrolidone.

Clause 19: The method of clause 17 or 18, wherein curing the top coat precursor comprises thermal curing, and wherein the top coat precursor comprises water, and wherein the top coat precursor comprises, per 100 weight units of water, between about 0.4 and about 40 weight units of sodium hyaluronate, between about 0.02 and 0.2 weight units of aziridine, and between 0.02 and 0.1 weight units of a surfactant.

Clause 20: The method of any of clauses 13 to 16, wherein curing the base coat precursor comprises ultraviolet (UV) curing, and wherein the base coat precursor comprises a solvent, and per 100 weight units of the solvent, about 1.5 weight units of ethyl acrylate, about 1.5 weight units of a polyolefin elastomer, about 1 weight unit of N-vinyl pyrrolidone, and about 0.1 weight units of a UV photoinitiator.

Clause 21: The method of clause 20, wherein curing the top coat precursor comprises UV curing, and wherein the top coat precursor comprises water, and per 100 weight units of water, between about 0.2 and about 20 weight units of sodium hyaluronate, about 0.5 weight units of aziridine, about 10 weight units of polyvinyl methyl ether maleic anhydride, and between about 0.01 and about 0.05 weight units of the UV photoinitiator.

Clause 22: The method of any of clauses 13 to 16, wherein curing the base coat precursor comprises thermal curing, wherein curing the top coat precursor comprises thermal curing, wherein the base coat precursor comprises propylene glycol methyl ether acetate (PGMEA) as solvent, wherein the base coat precursor comprises, per 95 weight units of PGMEA, about 2 weight units of a 2% weight/volume solution of a styrene-isoprene thermoplastic elastomer ethyl acrylate in acetone, about 2 weight units of ethyl acrylate, and about 1 weight unit of 900 Dalton polyethylene oxide dissolved in methanol, wherein the top coat precursor comprises water as solvent, and wherein the top coat precursor comprises, per 100 weight units of water, about 2 weight units of sodium hyaluronate, about 0.05 weight units of aziridine, about 0.05 weight units of a surfactant, and about 2 weight units of 900 Dalton polyethylene oxide dissolved in methanol.

Clause 23: The method of any of clauses 13 to 22, wherein the compliant hydrophilic coating exhibits substantially no cracking or flaking in in response to an expansion of the flexible substrate to 500% of an original size of the flexible substrate.

Clause 24: The method of any one of claims 13 to 23, wherein the medical device comprises a balloon comprising the flexible substrate.

Clause 25: The method of any of clauses 13 to 24, wherein the medical device comprises an elongated member comprising the flexible substrate.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Medical devices may include flexible, deformable, or expandable substrates, for example, balloons, stents, stent-grafts, wires, sheaths, or catheter shafts. Such medical devices may be provided with coatings, for example, to facilitate transport through body lumens, to provide lubricity, to improve biocompatibility, or for other applications. For example, to render a medical device more slippery, the device surfaces may be coated with low-friction materials, such as lubricious materials. Slippery components such as balloons and catheter shafts may improve navigation, for example, in a tight or constrained bend of a vasculature. However, such coatings may crack, peel, flake, disintegrate, or deteriorate during operation of the medical device, for example, in response to deformation, elongation, expansion, or flexure of a substrate or component of the medical device provided with the coating.

Compliant hydrophilic coatings according to the disclosure may exhibit reduced or substantially no cracking, peeling, or flaking in response to deformation, flexure, or expansion of a flexible substrate coated with the coatings, e.g., in response to deformation, flexure, or expansion of a flexible substrate coated with the coatings less than a threshold amount. A relatively compliant coating (also called a compliant coating) is a coating that deforms in response to a deformation of a substrate on which the coating is applied, without resulting in substantial mechanical failure or substantial loss of integrity of the coating. Thus, deformable or expandable medical devices, for example, balloons, stents, stent-grafts, wires, sheaths, or catheter shafts may be provided with hydrophilic coatings that conform to surfaces of the medical devices and substantially retain integrity during use or deployment.

The compliant hydrophilic coatings described herein may include a base coat and a lubricious top coat. The base coat may include a copolymer of a thermoplastic elastomer and ethyl acrylate. The base coat may contribute to adhesion of the lubricious top coat to an underlying substrate, and may be relatively elastic, enabling the deformation of the compliant hydrophilic coating while reducing or substantially eliminating cracking, peeling, or flaking of the compliant hydrophilic coating.

Figure 1:
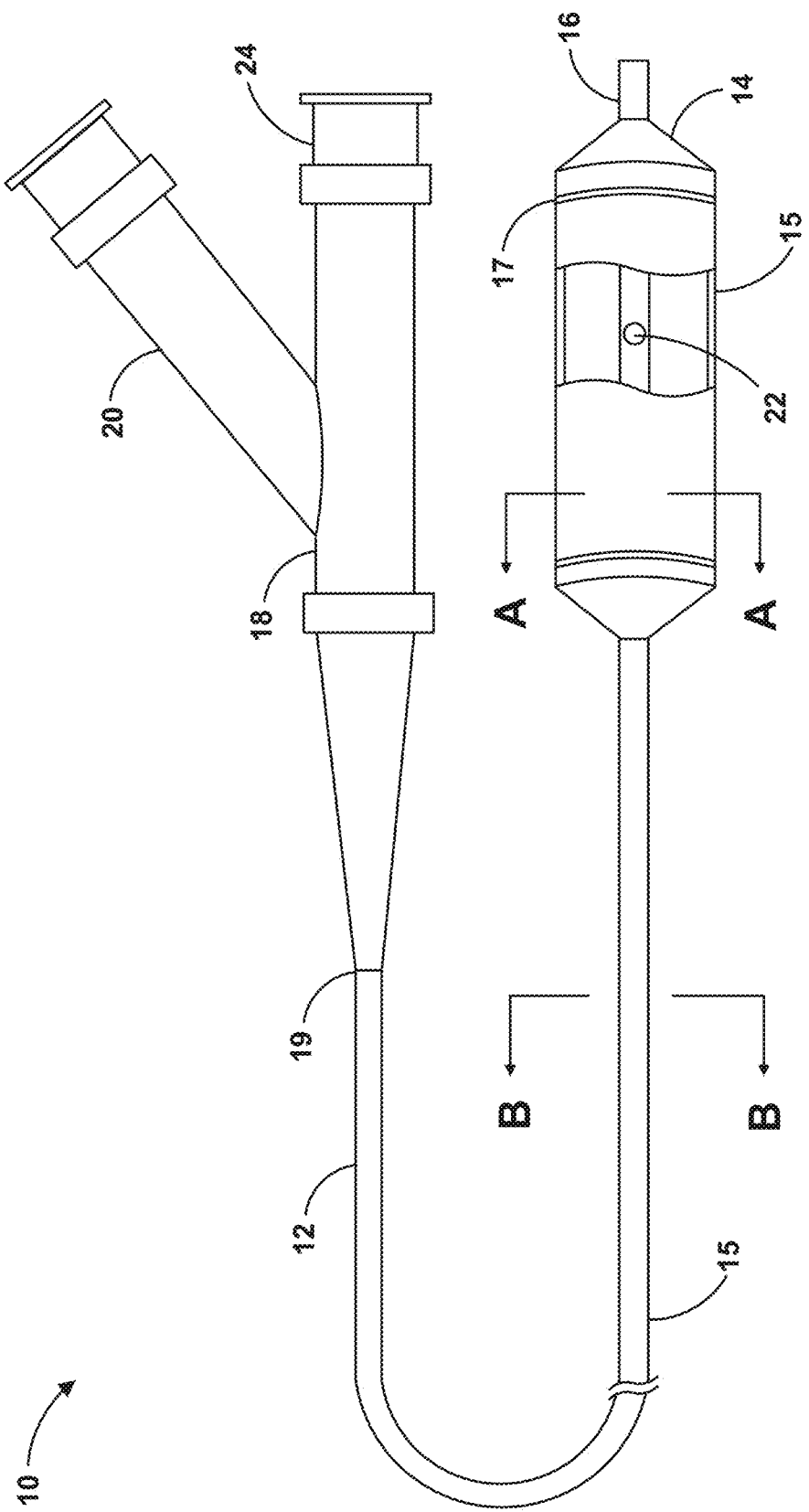
FIG. 1 is a schematic and conceptual side view of an example medical device including an elongated member and a balloon coated with a hydrophilic compliant coating.

FIG. 1 is a schematic and conceptual side view of an example medical device 10 including an elongated member 12 and a balloon 14. One or both of elongated member 12 or balloon 14 may be coated with a compliant hydrophilic coating 15 (also referred to as "coating 15" in the disclosure). In some examples, balloon 14 is mounted or secured to elongated member 12. For example, balloon 14 may be mounted closer to a distal tip 16 of elongated member 12 than a proximal end 19 of elongate member 12.

Medical device 10 also may include a hub 18. Hub 18 may be connected to the proximal end of elongated member 12 to allow elongated member 12 to be manipulated, advanced, or retracted, e.g., within a body lumen of a patient, and may provide one or more ports for communicating with one or more corresponding lumens defined in elongated member 12. For example, hub 18 may include an inflation arm 20 that may be connected to a source of inflating fluid and an inflation lumen defined in elongated member 12. Inflation arm 20 may allow inflating fluid to be delivered through an inflation lumen port 22 to inflate balloon 14, or withdrawn through inflation lumen port 22 to deflate balloon 14. In some examples, hub 18 may include an adapter 24 coupled to a guidewire lumen in elongated member 12 (not shown). This may allow medical device 10 to be advanced over the guidewire when inserting medical device 10 into a body lumen of a patient. In some examples, elongated member 12 may include a catheter body, for example, a balloon catheter, and hub 18 may include a catheter hub. In some examples, medical device 10 may omit balloon 14, and may include elongated member 12 including a catheter shaft. In some examples, medical device 10 may include a rapid-exchange balloon catheter system.

Elongated member 12 may be advanced to a target site, for example, through a body lumen such as vasculature of a patient. In some examples, distal tip 16 may be introduced into the body lumen of the patient through an incision or a natural or artificial opening, followed by a shaft of elongated member 12. Elongated member 12 may be advanced through the body lumen, for example, over a guidewire or another guide member (e.g., a guide catheter) disposed in a guidewire lumen of elongated member 12. In some examples, balloon 14 may be maintained in an uninflated or partly inflated configuration while advancing elongated member 12 through the vasculature. When elongated member 12 is sufficiently advanced, for example, such that balloon 14 is adjacent the target site, inflating fluid may be delivered through inflation lumen port 22 to inflate balloon 14 to an inflated configuration at the target site.

Balloon 14 is illustrated in an inflated configuration in FIG. 1. In some examples, inflation of balloon 14 may result in expansion of the vasculature, or removal of blockage, for example, clots, debris, or fat at the target site. The inflating fluid may subsequently be withdrawn through inflation lumen port 22 to result in deflation of balloon 14, and deflated balloon 14 may be withdrawn through the vasculature by retracting elongated member 12, e.g., by actuating or manipulating hub 18.

In some examples, balloon 14 may include one or more radiopaque markers 17. For example, radiopaque marker 17 may include one or more radiopaque bands disposed about balloon 14 (and/or about elongated member 12 at or near one or both ends of balloon 14), such as one marker 17 adjacent the proximal end of balloon 14 and another marker 17 adjacent a distal end of balloon 14, as shown in FIG. 1. Radiopaque marker 17 may allow a clinician to observe the position of balloon 14 using suitable radio-imaging techniques during a medical procedure, for example, while advancing or retracting balloon 14 and elongated member 12.

Figure 2:
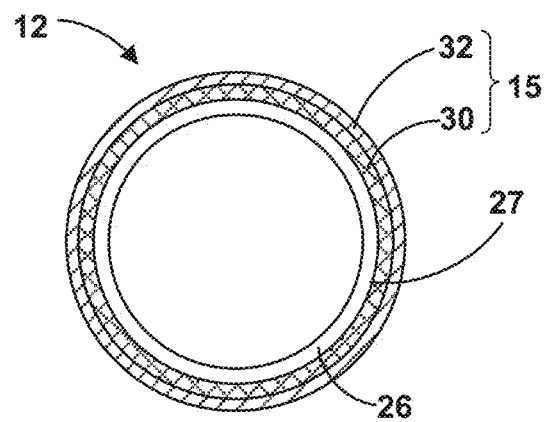
FIG. 2 is a schematic and conceptual cross-sectional view of the example elongated member of FIG. 1.

FIG. 2 is a schematic and conceptual cross-sectional view of elongated member 12 of FIG. 1, taken along section B-B of FIG. 1. As seen in FIG. 2, elongated member 12 may be defined by a flexible substrate 26. Flexible substrate 26 may provide elongated member 12 with a predetermined deformability, for example, bendability, flexibility, expandability, or the like. Flexible substrate 26 may be formed from any suitable material, for example, a biocompatible polymeric material. The polymeric material may include a thermoplastic, an elastomer, or an elastomeric thermoplastic. In some examples, flexible substrate 26 may include one or more of polyurethanes, thermoplastic polyurethanes, polyamides, for example, nylons, polyamide 6 (PA 6), or polyamide 66 (PA 66), polyolefins, polyethylenes (for example, high density polyethylene (HDPE) or low density polyethylene (LDPE)), polypropylenes (PP), polyethylene terephthalate (PET), fluoropolymers, polytetrafluoroethylene (PTFE), polyetheretherketone (PEEK), vinyls, silicones, or polyimides. While flexible substrate 26 may not be inflated or expanded during operation, manufacturing and operational tolerances for elongated member 12 may be determined in terms of inflation or expansion of flexible substrate 26. For example, coating 15 may be provided with a predetermined compliance or integrity such that coating 15 substantially retains integrity in response to a test inflation or expansion of flexible substrate 26, Thus, in some examples, medical device 10 includes an elongated member 12 including flexible substrate 26.

Figure 3:
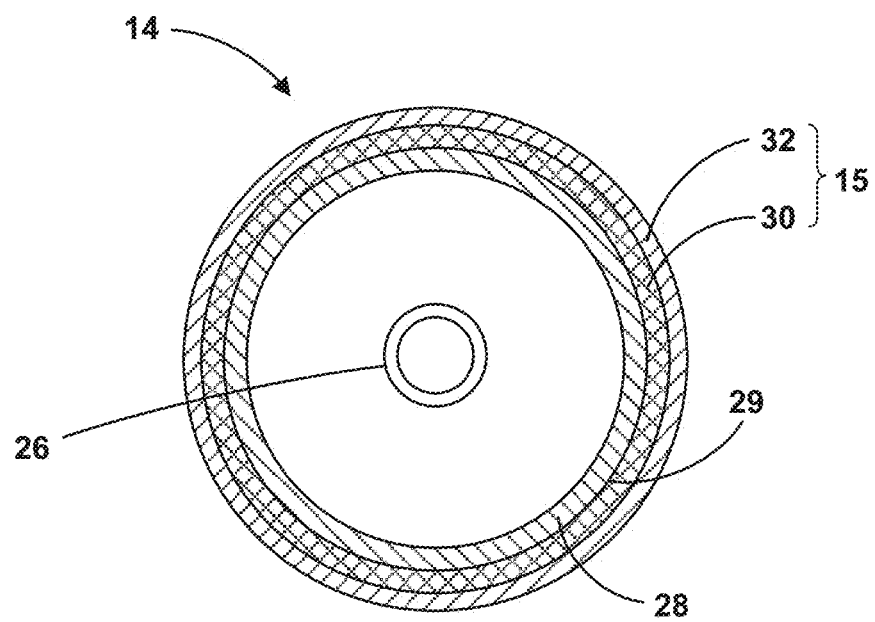
FIG. 3 is a schematic and conceptual cross-sectional view of the example balloon of FIG. 1

FIG. 3 is a schematic and conceptual cross-sectional view of balloon 14 of FIG. 1, taken along section B-B of FIG. 1. As shown in FIG. 3, balloon 14 may be defined by a balloon wall 28. Balloon wall 28 may include a flexible substrate providing balloon 14 with predetermined inflatability, compliance, or flexibility. For example, balloon 14 may be inflatable to a predetermined inflated volume, and may not be substantially further inflatable beyond the predetermined inflated volume, e.g., without damage to balloon wall 28. Balloon wall 28 may include one or more layers. Thus, in some examples, balloon 14 may include a single-layer balloon wall 28, while in other examples, balloon 14 may include a multi-layer balloon wall 28.

One or more layers of balloon wall 28 of balloon 14 may be formed of an inflatable material, for example, a polymer material that reversibly expands when subject to an inflation pressure. One or more layers of balloon wall 28 may have the same, similar, or different compositions, and have the same, similar, or different inflation characteristics. For example, at least one layer of balloon 14 may include one or more of a thermoplastic, an elastomer, or an elastomeric thermoplastic. In some examples, balloon wall 28 may include one or more of acrylonitrile-butadiene styrene (ABS), polyamides, for example, nylons, polyamide 6 (PA 6), or polyamide 66 (PA 66), polyethylenes (for example, high density polyethylenes (HDPE) or low density polyethylenes (LDPE)), poly(methyl methacrylate) (PMMA), polyoxymethylene (POM,), polybutylene terephthalate (PBT), styrene acrylonitrile resin (SAN), thermoplastic elastomers (TPE) (for example, polyether block amides (PEBAs)), polyester block ethers, polyethylene terephthalate, polyurethanes, polyesters, styrene ethylene butylene styrene (SEBS), styrene-butadiene-styrene (SBS), ChronoPrenem™ (AdvanSource Biomaterials, Wilmington, Mass.), ChronoPrene™ 5A, ChronoPrene™ 15A, C-FLEX® (Saint-Gobain, Akron, Ohio), Kraton (Kraton Corporation, Houston, Tex.) or blends, copolymers, or coextrusions thereof. In some examples, the TPEs (or PEBAs) may include materials sold under the PEBAX® brand name (Arkema., Paris, France) or VESTAMID® (Evonik Industries, Essen, Germany). In some examples, the thermoplastic may include materials sold under the GRILAMID® brand name (EMS-Grivory, Domat/Ems, Switzerland), which includes amide thermoplastics.

While in the example shown in FIG. 3, balloon 14 is illustrated having a circular cross-section, in other examples, balloon 14 may have any suitable shape, configuration, or cross-sectional shape. In some examples, balloon 14 may have a geometrically similar shape in an uninflated and an inflated configuration. For example, balloon 14 may be cylindrical in both uninflated and inflated configurations. In some examples, balloon 14 may have different shapes in uninflated and inflated configurations. For example, balloon 14 may be folded or otherwise have a compact uninflated configuration and may define a cylindrical or another shape in an inflated configuration.

Compliant hydrophilic coating 15 may be provided on a at least a portion of a flexible substrate of medical device 10. For example, medical device 10 may include a first flexible substrate 26 defining elongated member 12, or a second flexible substrate 28 defining balloon 14. First and second flexible substrates 26 and 28 respectively define first and second major surfaces 27 and 29, for example, exterior surfaces defined by elongated member 12 or balloon 14 respectively. In some such examples, compliant hydrophilic coating 15 may at least partially cover one or both of first and second major surfaces 27 or 29. In some examples, flexible substrate 28 of balloon 14 may be coated with compliant hydrophilic coating 15 and flexible substrate 26 of elongated member 12 may not be coated with compliant hydrophilic coating 15.

Compliant hydrophilic coating 15 may provide one or more of lubricity, biocompatibility, hydrophilicity, anti-thrombogenicity, or protection to elongated member 12 or balloon 14. Compliant hydrophilic coating 15 may be compliant and flexible. For example, coating 15 may exhibit substantially no cracking or flaking in in response to an expansion of a flexible substrate on which compliant hydrophilic coating 15 is provided, up to a predetermined extent, for example, 500% of an original size of the flexible substrate.

As seen in FIGS. 2 and 3, compliant hydrophilic coating 15 can include a base coat (or layer) 30 and a lubricious top coat (or layer) 32. In some examples, base coat 30 may provide one or more of strength, compliance, flexibility, or integrity to compliant hydrophilic coating 15, by promoting uniform adherence and retention of lubricious top coat 32 along a surface of a flexible substrate to which compliant hydrophilic coating 15 is applied, compared to a coating without a base coat. The thickness of base coat 30 may be adjusted to provide a predetermined average thickness to compliant hydrophilic coating 15, for example, to modify the strength, compliance, flexibility, or integrity of compliant hydrophilic coating 15. For example, base coat 30 may have a thickness between about 2 and about 30 µm. Thus, even in examples in which the thickness of lubricious top coat 32 may be constrained by a maximum thickness (for example, in view of integrity or durability of lubricious top coat 32), the thickness of compliant hydrophilic coating 15 may be adjusted beyond the maximum thickness by providing a predetermined thickness to base coat 30. In some examples, lubricious top coat 32 may have a thickness between about 1 and about 15 µm. In some examples, compliant hydrophilic coating 15 may have a thickness between about 3 and about 45 µm.

In some examples, base coat 30 includes a copolymer of a thermoplastic elastomer and ethyl acrylate. For example, the copolymer may be formed from a precursor composition including between about 0.5 wt. % and about 20 wt. % of the thermoplastic elastomer. In some examples, the copolymer may be formed from a precursor composition including about 0.5 wt. % and about 2 wt. % of ethyl acrylate. Using a thermoplastic elastomer as a copolymer component in base coat 30 may provide coating 15 with one or more of a predetermined compliance, flexibility, durability, or integrity. In some examples, the thermoplastic elastomer includes at least one of a styrene-isoprene thermoplastic elastomer or a polyolefin elastomer. For example, the thermoplastic elastomer may include a styrene-ethylene-butylene-styrene (SEBS), a polyurethane, ChronoPrene™ (AdvanSource Biomaterials, Wilmington, Mass.), ChronoPrene™ 5A, ChronoPrene™ 15A, C-FLEX® (Saint-Gobain, Akron, Ohio), or the like. In some examples, the polyolefin elastomer may include an ethylene-octene copolymer, for example, ENGAGE™ Polyolefin Elastomers (Dow Chemical Company, Midland, Mich.), ENGAGE™ 8107, 7367, 7270, or the like. In some examples, base coat 30 includes a polymer formed by drying, curing, or crosslinking one or more of ethyl acrylate, PEO, pyrrolidone, hydroxyethyl methacrylate, hexamethylene diisocyanate, hydrophilic polyether aliphatic polyurethane (for example, Hydrothane, AdvanSource Biomaterials Wilmington, Mass.), or HydroMed D-640 (AdvanSource Biomaterials Wilmington, Mass. permanently lubricious polyurethane granules. For example, the polymer may be formed from a precursor including between about 0.1 wt. % and about 5 wt. % of one or more monomeric or oligometic components.

In some examples, base coat 30 further includes at least one of polyethylene oxide (PEO) or N-vinyl pyrrolidone. Providing PEO or N-vinyl pyrrolidone in base coat 30 may provide base coat 30 with pliability, compliance, or flexibility.

Lubricious top coat 32 may include a biocompatible, lubricious polymeric material. For example, lubricious top coat 32 may include a biocompatible, hydrophilic polymeric material. In some examples, lubricious top coat 32 includes sodium hyaluronate and aziridine. Sodium hyaluronate may provide lubricity and hydrophilicity, while azaridine may be a cross-linker. In some examples, instead of, or in addition to, sodium hyaluronate or azaridine, lubricious top coat 32 may include at least one polymer selected from a group consisting of polyvinylpyrrolidone, polyethylene oxide, polypropylene oxide, polyacrylamide, soft polyurethane with durometer less than 80A (for example, Elasthane 80A or Tecothane Soft AR-62A, Lubrizol, Wickliffe, Ohio), methyl cellulose, polyacrylic acids, and polyvinyl alcohols. In some examples, lubricious top coat 32 may include at least one of polyvinyl methyl ether, maleic anhydride, low durometer polyether block amide (for example, PEBAX 2533), or copolymers thereof in 2:1 or another ratio co-dissolved in an appropriate solvent system for example, acetone/tetra hydrofuran (THF), or dimethyl acetamide (DMA), alone or mixed with ketones or aromatic solvents. In some examples, lubricious top coat 32 may optionally include a surfactant. For example, the surfactant may include non-ionic surfactants with long chain alcohols such as fatty alcohols, cetyl alcohols or cationic surfactant, such as IGEPAL CO-520 (Sigma-Aldrich, St. Louis, Mo.) or anionic surfactant contains highly polar anionic group including polyether groups including ethoxylated polyethylene oxide-like sequences inserted to increase the hydrophilic character. In some examples, polypropylene oxides may be inserted to increase the lipophilic property. The surfactant may promote homogeneity and uniformity of the composition within lubricious top coat 32. In some examples, lubricious top coat 32 may include a composition formed by drying and/or curing a composition including sodium hyaluronate, aziridine, and a surfactant. In some other examples, lubricious top coat 32 may include a composition formed by drying and/or curing a composition including sodium hyaluronate, aziridine, a surfactant, and polyethylene oxide. In some other examples, lubricious top coat 32 may include a UV radiation-cured composition formed by UV radiation curing a liquid composition including sodium hyaluronate, polyfunctional aziridine cross-linker, for example, Neocryl CX-100 (DSM Coating Resins, Wilmington, Mass.) (for example, ranging between about 0.01 wt. % and about 0.1 wt. %), polyvinyl methyl ether maleic anhydride (PVM-MA), and a UV photoinitiator. In some examples, the composition includes between about 0.1 wt. % and about 5 wt. % of the photoinitiator. In some examples, the photoinitiator includes Irgacure 369 (BASF, Florham Park, N.J.). The composition may include one or more of acrylate or styrene-based formulations, photo-polyvinylpyrrolidone, or photo-polyacrylamide.

Figure 4:
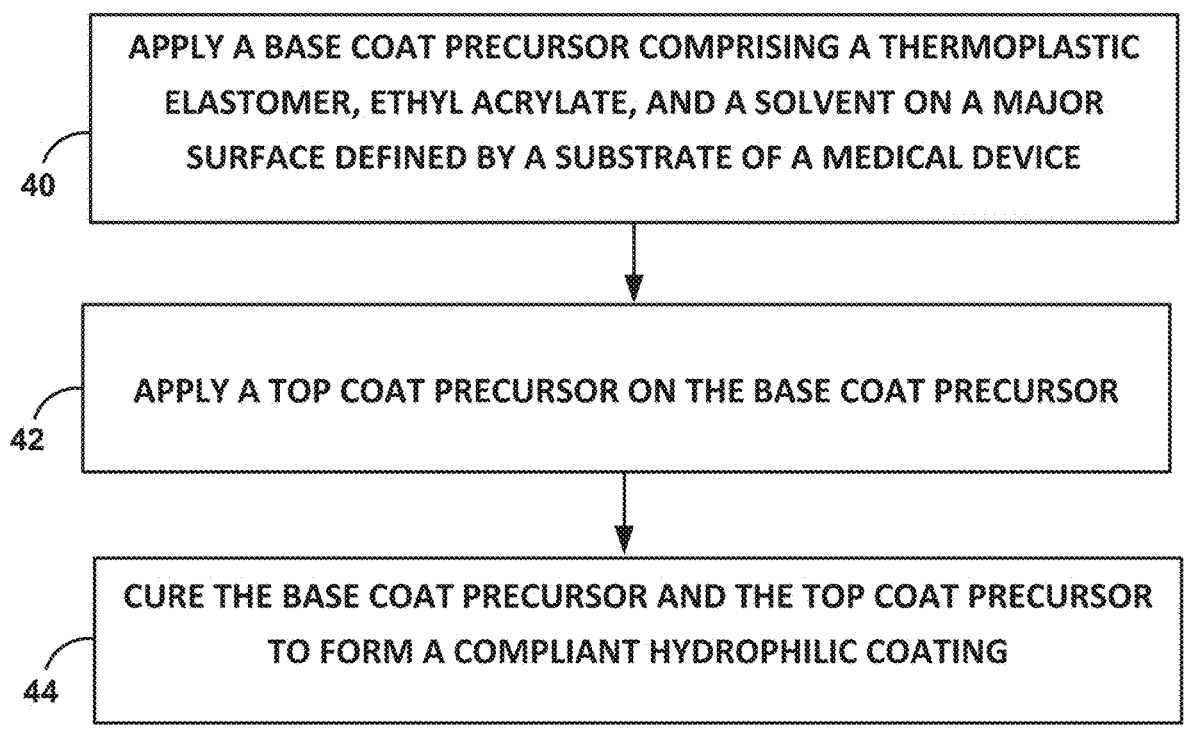
FIG. 4 is a flow diagram of an example technique for coating a substrate of a medical device including an elongated member or a balloon with a hydrophilic compliant coating.

FIG. 4 is a flow diagram of an example technique for coating a substrate of medical device 10 including elongated member 12, balloon 14, or both with compliant hydrophilic coating 15, While the example technique of FIG. 4 is described with reference to example medical device 10 of FIG. 1, elongated member 12 of FIG. 2, and balloon 14 of FIG. 3 example techniques according to the disclosure may be used to provide a compliant hydrophilic coating 15 on any suitable medical device (including any of those mentioned herein) or article.

The example technique of FIG. 4 includes applying a base coat precursor including a thermoplastic elastomer, ethyl acrylate, and a solvent on a major surface defined by a substrate of medical device 12 (40). For example, the major surface may include one or both of first or second major surfaces 27 and 29. The base coat precursor may be applied using any suitable technique, for example, spraying, dip-coating, immersion coating, brushing, or rolling, that may be used for applying a coating on a substrate.

In some examples, applying the base coat precursor (40) includes dipping the substrate, for example, elongated member 12, balloon 14, or both into a solution of the base coat precursor for about 5 to 20 seconds, and removal of the substrate at a predetermined speed, for example, 0.2 to 1.5 inches per second. In other examples, applying the base coat precursor (40) may include moving a crucible (or other container configured to receive the substrate at least partially within a volume of coating material) containing the base coat precursor along a stationary substrate at a fixed or variable speed to apply desired coating thickness to elongated member 12, balloon 14, or both. After applying the base coat precursor (40), most solvent of the precursor may be allowed to evaporate at room temperature, for example, for about 5 to 30 minutes. To complete removal of solvent, the coated device may be heated (for example, in an oven) at an elevated temperature, such as about 60° C., for about 2 to 30 minutes, depending on coating thickness, to remove the solvent.

The example technique also includes applying a top coat precursor on the base coat precursor (42). The applying of the top coat precursor (42) may be performed using the same technique for applying the base coat precursor (40) or a different suitable technique. For example, both the base coat precursor and the top coat precursor may be applied by dip-coating or by spray-coating. In other examples, the top coat precursor may be applied by a different technique than the base coat precursor. In some examples, the base coat precursor may be sufficiently viscous or stable such that the top coat precursor can be applied to the base coat precursor without requiring curing of the base coat precursor. In other examples, the base coat precursor may first be cured to form base coat 30 before top coat precursor is applied. In some examples, the base coat precursor may be partly cured to provide sufficient stability or support for a subsequent coating, following by applying the top coat precursor (42). Thus, the top coat precursor may be applied over the base coat precursor, over partially cured base coat precursor, or over cured base coat 30.

The example technique includes curing at least one of the base coat precursor and the top coat precursor (44). The curing (44) may include simultaneous curing of both the base coat precursor and the top coat precursor, or may include separate curing of the base coat precursor and the top coat precursor. For example, the base coat precursor may be at least partly or substantially cured, before applying the top coat precursor (42).

Thus, one or both of base coat 30 or lubricious top coat 32 may be prepared by curing the base coat precursor or the top coat precursor respectively. The curing (44) may include one or more of thermal, chemical, or ultraviolet (UV) curing.

For example, the respective precursor may cure (at least partially cross-link) or substantially cure (substantially cross-link) in response to heat or exposure, exposure to a chemical reagent, or by mixing a two-part or multi-part chemically curable composition that cures by chemical reaction between different parts. The respective precursors may include components, for example, solvents, that may not be present in the cured coatings. For example, some components may be removed by evaporation, drying, volatilization, disintegration, thermal sacrifice, or the like.

In some examples, curing of the base coat precursor or of the top coat precursor (44) including thermal curing. The thermal curing may include exposing a respective precursor to a heated environment or fluid, for example, heated air, nitrogen, or another medium, or infrared heating, or resistive heating, or convective heating, or any other technique for heating the respective precursor to a predetermined curing temperature. The curing temperature may be maintained for a predetermined curing period. In some examples, at least part of the thermal curing may be simultaneous with UV curing. Thus, during the heating, or maintenance at the curing temperature, the respective precursor may be exposed to predetermined wavelengths, for example, UV wavelengths.

In some examples, curing (44) includes thermal curing, and base coat 15 is a product of thermal curing of the base coat precursor comprising a solvent. In some such examples, the base coat precursor may include, per 100 weight units of the solvent, about 2 weight units of ethyl acrylate, about 2 weight units of a styrene-isoprene thermoplastic elastomer, and about 1 weight unit of polyethylene oxide. In other such examples, the base coat precursor includes, per 100 weight units of the solvent, about 2 weight units of ethyl acrylate, about 2 weight units of a styrene-isoprene thermoplastic elastomer, about 2 weight units of a polyolefin elastomer, and about 1 weight unit of N-vinyl pyrrolidone.

In some examples, the base coat precursor includes a copolymer of a thermoplastic elastomer and ethyl acrylate, and further includes at least one of polyethylene oxide or N-vinyl pyrrolidone. In some such examples, the thermoplastic elastomer in the base coat precursor includes at least one of a styrene-isoprene thermoplastic elastomer or a polyolefin elastomer.

In examples where the base coat precursor includes a solvent, the solvent may include one or more of propylene glycol methyl ether acetate (PGMEA), chlorinated solvents, esters, ketones, aliphatic hydrocarbons, aromatic hydrocarbons, tetra hydro furan, or any suitable solvent for dissolving the copolymer components. In some examples, particular components of the base coat precursor may initially be dissolved in a first solvent before being mixed into the base precursor composition. For example, a styrene-isoprene thermoplastic elastomer resin or a polyolefin elastomer resin may be dissolved in one or more of hexane, chloroform, or carbon tetrachloride, or another appropriate solvent, before being mixed with other components to form the base coat precursor. The base coat precursor may include one or more of between about 10% and about 40% by weight of ethyl acrylate, between about 10% and about 20% by weight of PEO or N-vinyl pyrrolidone, between about 5% and about 10% by weight of hydroxyethyl methacrylate, or between about 0.5% and 5% by weight of polymeric hexamethylene diisocyanate (Desmodur N-100 or N-75, Covestro, Shanghai, China).

In some examples, the base coat precursor may include hydrophilic polyether aliphatic polyurethane (for example, Hydrothane, AdvanSource Biomaterials Wilmington, Mass.). In some such examples, the solvent may be selected from the group consisting of alcohols, chlorinated solvents, esters, ketones, aliphatic hydrocarbons, aromatic hydrocarbons, and mixtures thereof. In some examples, the base coat precursor may include HydroMed D-640 (AdvanSource Biomaterials Wilmington, Mass.) permanently lubricious polyurethane granules between about 1% and about 5% by weight in 95/5 ethanol/water or an organic solvent, for example, one or more of chlorinated solvents, esters, ketones, aliphatic hydrocarbons, aromatic hydrocarbons, dimethyl acetatnide (DMA), PM acetate and mixtures thereof.

In some examples, the top coat precursor includes sodium hyaluronate and azaridine, or at least one polymer selected from a group consisting of polyvinylpyrrolidone, polyethylene oxide, polypropylene oxide, polyacrylamide, methyl cellulose, polyacrylic acids, and polyvinyl alcohols.

In some examples, curing (44) includes thermal curing, and lubricious top coat 32 is a product of thermal curing of the top coat precursor comprising water. In some such examples, the top coat precursor may be heated to a predetermined curing temperature, for example, between about 120° F. (about 49° C.) and about 180° F. (about 82° C.). The curing time may range, for example, between about 1 hour and about 4 hours.

In some examples, the top coat precursor includes, per 100 weight units of water, between about 0.4 and about 40 weight units of sodium hyaluronate, between about 0.02 and 0.2 weight units of aziridine, and between 0.02 and 0.1 weight units of a surfactant. In some examples, lubricious top coat 32 may include between about 90% and about 99% by weight of sodium hyaluronate in water, and between about 0.1% to about 2% by weight of azaridine or another cross-linker.

In some examples in which curing (44) of both the base coat precursor and the top coat precursor includes thermal curing, base coat 30 may be a product of thermal curing of a base coat precursor comprising propylene glycol methyl ether acetate (PGMEA) as solvent, and lubricious top coat 32 may be a product of thermal curing of a top coat precursor comprising water as solvent. In some such examples, the base coat precursor may include, per 95 weight units of PGMEA, about 2 weight units of a 2% weight/volume solution of a styrene-isoprene thermoplastic elastomer ethyl acrylate in acetone, about 2 weight units of ethyl acrylate, and about 1 weight unit of 900 Dalton polyethylene oxide dissolved in methanol, and the top coat precursor may include, per 100 weight units of water, about 2 weight units of sodium hyaluronate, about 0.05 weight units of aziridine, about 0.05 weight units of a surfactant, and about 2 weight units of 900 Dalton polyethylene oxide (PEO) dissolved in methanol. Providing the surfactant may promote formation of a uniform and homogenous coating by promoting the uniform dispersion of components of the coating. The PEO may provide a rubbery lubricious characteristic to lubricious top coat 32.

In some examples, curing (44) of at least one of the base coat precursor and curing (42) of the top coat precursor includes ultraviolet curing. The ultraviolet curing may include exposure of the respective precursor to a predetermined magnitude or power of light including predetermined UV wavelengths for a predetermined curing time. In some such examples, the respective precursor may include a UV photoinitiator to initiate or promote UV curing. For example, curing (44) may include ultraviolet (UV) curing, and base coat 30 may be a product of UV curing of the base coat precursor comprising a solvent. In some such examples, the base coat precursor may include, per 100 weight units of the solvent, about 1.5 weight units of ethyl acrylate, about 1.5 weight units of a polyolefin elastomer, about 1 weight unit of N-vinyl pyrrolidone, and about 0.1 weight units of a UV photoinitiator.

In some examples, curing (44) includes ultraviolet (UV) curing, and lubricious top coat 32 may be a product of UV curing of a top coat precursor comprising water. The UV cure period may range between about 30 to about 120 seconds. In some such examples, the top coat precursor may include, per 100 weight units of water, between about 0.2 and about 20 weight units of sodium hyaluronate, about 0.5 weight units of aziridine, about 10 weight units of polyvinyl methyl ether maleic anhydride, and between about 0.01 and about 0.05 weight units of the UV photoinitiator.

The curing (44) forms compliant hydrophilic coating 15 including base coat 30 at least partially covering the substrate and lubricious top coat 32 on base coat 30. For example, the substrate may include flexible substrate 26 of elongated member 12 or balloon wall 28 of balloon 14. Thus, compliant hydrophilic coating 15 according to the disclosure may thus be formed using example techniques described with reference to FIG. 4. However, compliant hydrophilic coating 15 may be formed using any suitable technique.

After coating is cured (44), the coated device 10 may optionally be rinsed with a rinse solution to remove unreacted components or impurities. For example, the rinse solution may include water or a predetermined buffer solution. Such rinsing may provide better biocompatibility of coating 15. After curing (44), and after the optional rinsing, the coated device 10 may optionally be sterilized. For example, the coated device 10 may be exposed to ethylene oxide gas, or electron beam sterilization, or any other suitable sterilization technique.

Compliant hydrophilic coating 15 according to the disclosure may be a compliant hydrophilic coating that exhibits no cracking or flaking (or substantially no cracking or flaking) in response to an expansion of the flexible substrate up to a predetermined amount, such as 500% (or about 500%) of an original size of the flexible substrate. The expansion may be calculated by determining an initial dimension, for example, an initial radius or diameter, and a final dimension, for example, after expansion, and determining the % increase in the respective dimension. For example, an increase in a diameter of a tubing from 1 mm to 6 mm would correspond to an expansion of 500% (=100*(6−1)/1).

Cracking, flaking, or peeling of compliant hydrophilic coating 15 may be determined by using a deformation test. An initial number of cracks or flakes per unit area may be determined by visually inspecting a surface region of elongated member 12 or balloon 14 coated with compliant hydrophilic coating 15 may be examined in an undeformed configuration (for example, uninflated, unbent, unflexed, or unexpanded configurations). Elongated member 12 or balloon 14 may then be subjected to a deformation, for example, inflation, bending, flexing, or expanding. In some examples, the deformation may include expanding elongated member 12 or balloon 14 to an expanded diameter relative to an initial diameter, for example, up to 6 times the initial diameter, or an increase of 500% relative to the initial diameter. A final number of cracks or flakes per unit area may be determined by visually inspecting the same surface region of elongated member 12 or balloon 14. The % increase in the number of cracks or flakes may thus be determined. The % increase in cracks or flakes may be indicative of compliance or integrity of compliant hydrophilic coating 15, with a relatively lower % increase being indicative of a higher compliance and integrity, and a relatively higher % increase being indicative of a lower compliance and integrity of compliant hydrophilic coating 15.

Thus, compliant hydrophilic and lubricious coatings for medical devices are described that exhibit substantially none or reduced cracking, peeling, or flaking upon expansion of the flexible substrate up to a predetermined amount, such as about 500% of an original size of the coating or a substrate on which the coating is applied.

EXAMPLES

Comparative Example 1

Figure 5:
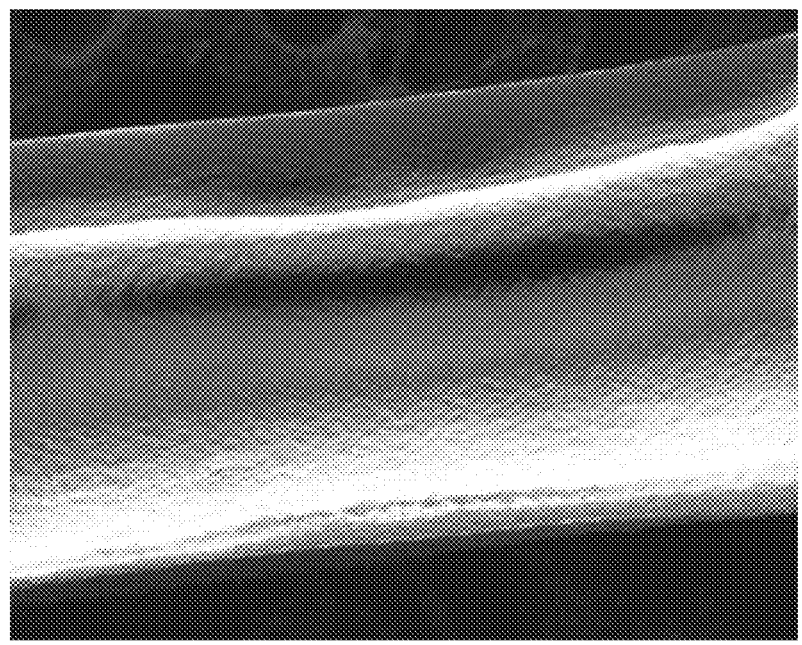
FIG. 5 is a photograph showing an uncoated balloon tubing made of a biocompatible thermoplastic elastomer.
Figure 6:
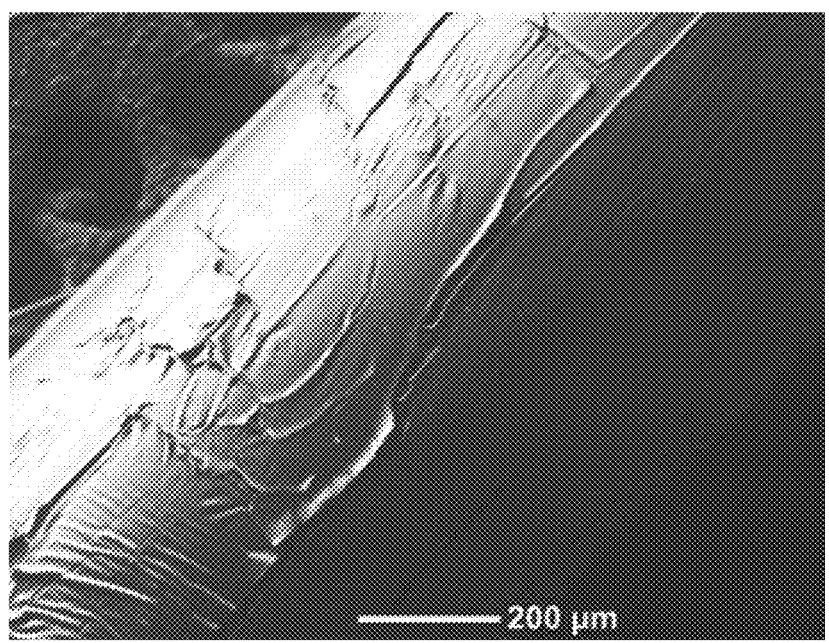
FIG. 6 is a photograph showing a balloon tubing made of a biocompatible thermoplastic elastomer coating with a comparative hydrophilic coating.
Figure 7:
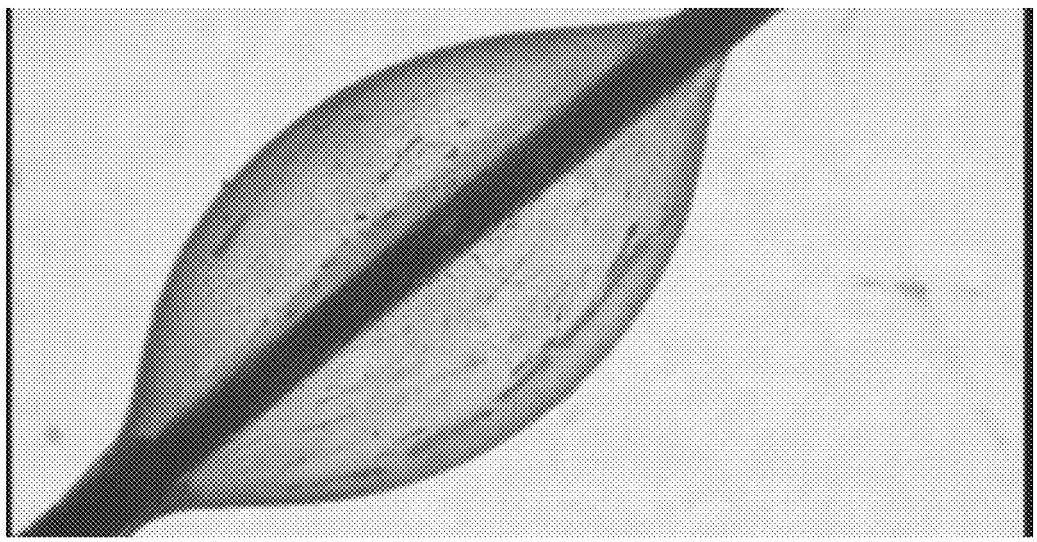
FIG. 7 is a photograph showing the balloon tubing of FIG. 6 inflated to 500%.
Figure 8:
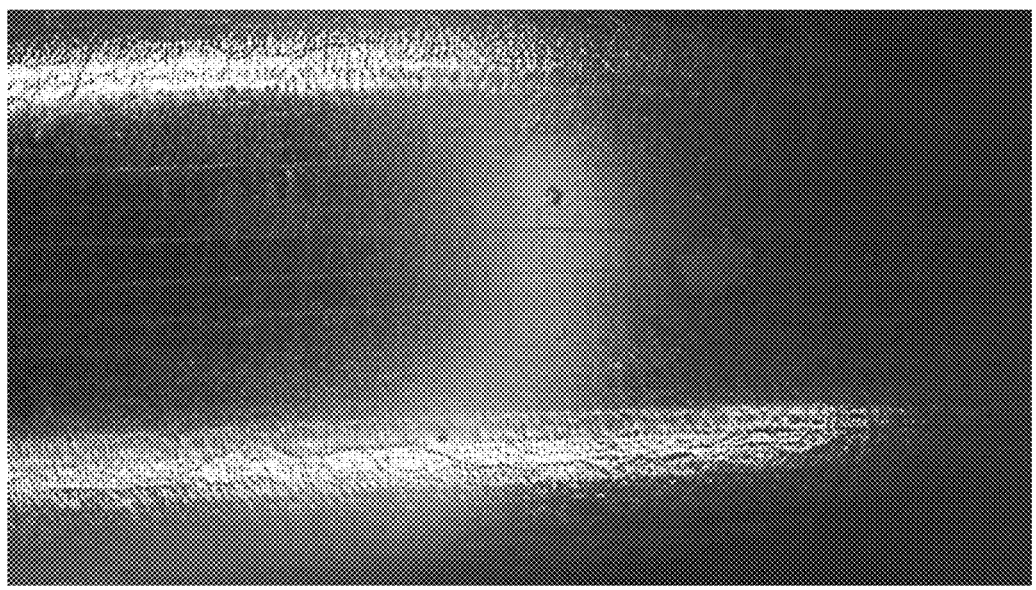
FIG. 8 is a photograph showing a post-inflation surface region of the balloon tubing of FIG. 6.
Figure 9:
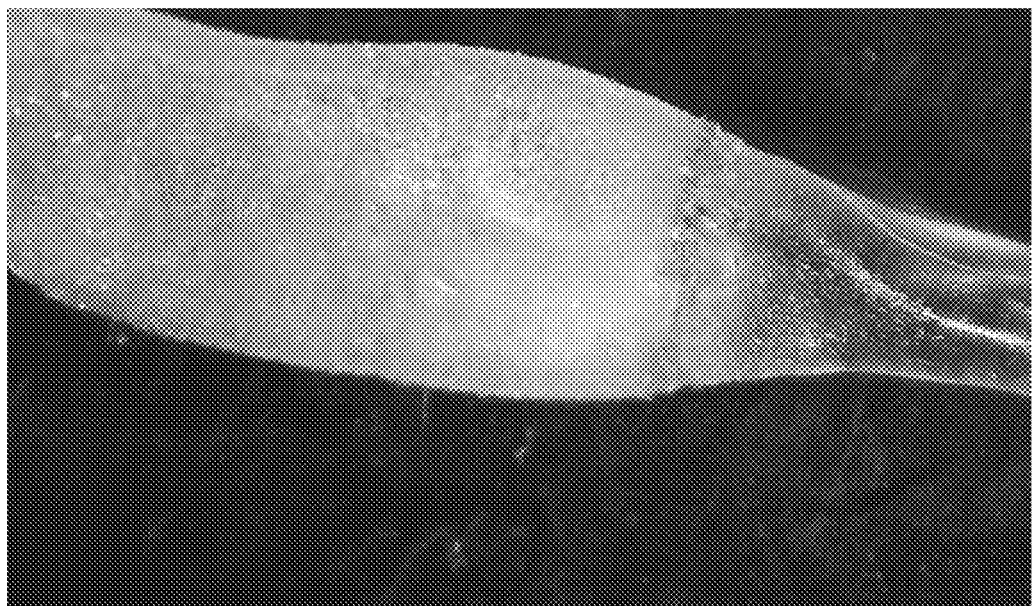
FIG. 9 is a photograph showing a post-inflation surface region of a balloon tubing coated with a comparative hydrophilic coating.

A conventional UV cured hydrophilic coating was made from the mixture of photo-polyvynylpyrrolidone, PVP, and photocrossliner as base coat. The top topcoat included photo-polyvynylpyrrolidone, photoacryamide, and photo-crosslinker under UV radiation for about 30 to 120 seconds. The base coat was applied and cured for 30 to 200 seconds on a medical device substrate first, then the top coat was applied and cured on the base coat. FIG. 5 is a photograph showing an uncoated balloon tubing made of a biocompatible thermoplastic elastomer (Chronoprene™, AdvanSource Biomaterials, Wilmington, Mass.). FIG. 6 is a photograph showing a balloon tubing made of a biocompatible thermoplastic elastomer coating with a comparative hydrophilic coating. FIG. 7 is a photograph showing the balloon tubing of FIG. 6 inflated to 500%. FIG. 8 is a photograph showing a post-inflation surface region of the balloon tubing of FIG. 6. FIG. 9 is a photograph showing a post-inflation surface region of a balloon tubing coated with the comparative hydrophilic coating of COMPARATIVE EXAMPLE 1. As seen in FIGS. 6, 7, 8, and 9, random irregular cracks and tear were observed after the tubing was inflated to 500% of its original size, defined with respect to a diameter of the tubing.

Example 1

An example compliant hydrophilic coating was formed on a medical device substrate by coating a base coat composition and a top coat composition. The base coat composition was prepared by dissolving 2 grams of a Chronoprene™ 15A (AdvanSource Biomaterials, Wilmington, Mass.) solution, 2 grams of ethyl acrylate, and 1 gram of 900 Dalton polyethylene oxide solution in 95 grams of propylene glycol methyl ether acetate (PGMEA). The Chronoprene 15A solution included 2 wt. % of Chronoprene™ 15A in acetone. The PEO solution included methanol as a solvent (5 to 20 wt. %). The top coat composition was prepared by dissolving 2 grams sodium hyaluronate, 0.05 grams of aziridine, 0.05 of a non-ionic surfactant, and 2 grams of the PEO solution in 100 grams of distilled water.

The base coat was applied to a Chronoprene™ tubing substrate. FIG. 5 is a photograph showing an uncoated balloon tubing made of a biocompatible thermoplastic elastomer (Chronoprene™). The base coat was dried and cured at 150° F. (66° C.) for 10 minutes. The top coat was then applied, followed by curing at 150° F. (66° C.) for 30 minutes.

Figure 10:
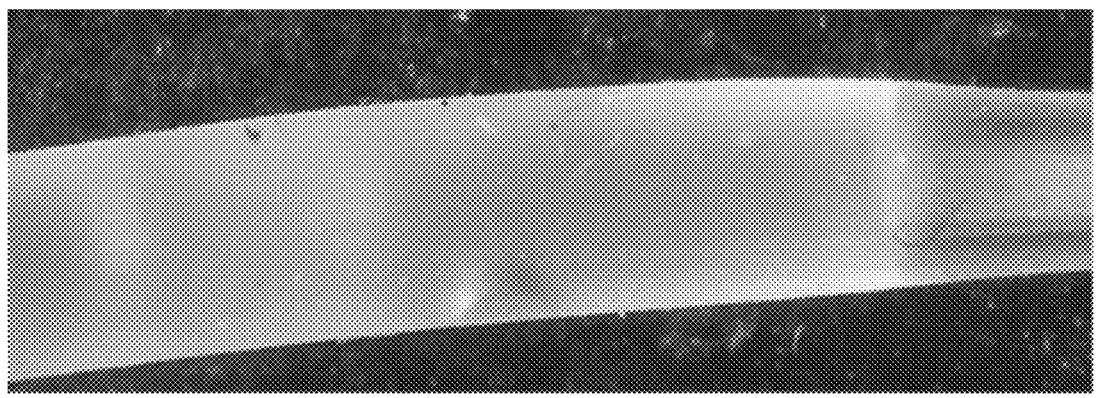
FIG. 10 is a photograph showing a post-inflation surface region of a balloon tubing coated with a base coat.
Figure 11A:
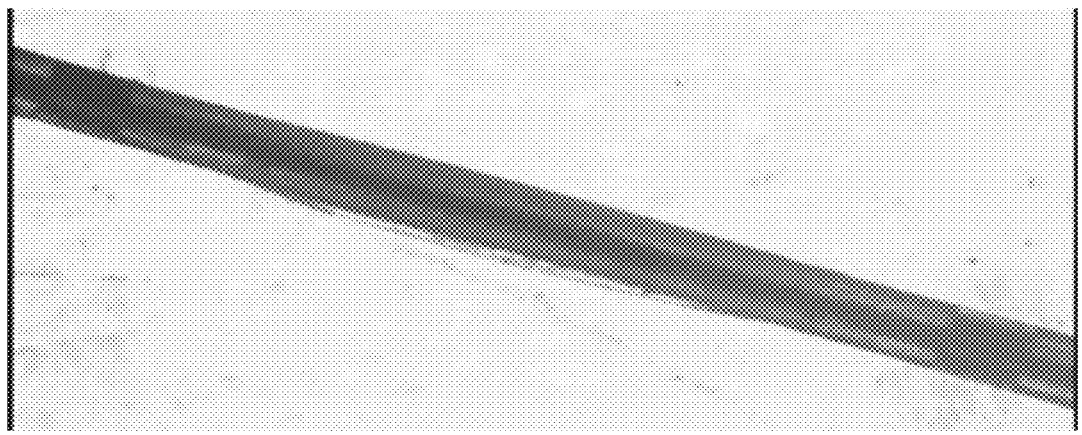
FIG. 11A is a photograph showing an uninflated balloon tubing coated with a base coat and a top coat.
Figure 11B:
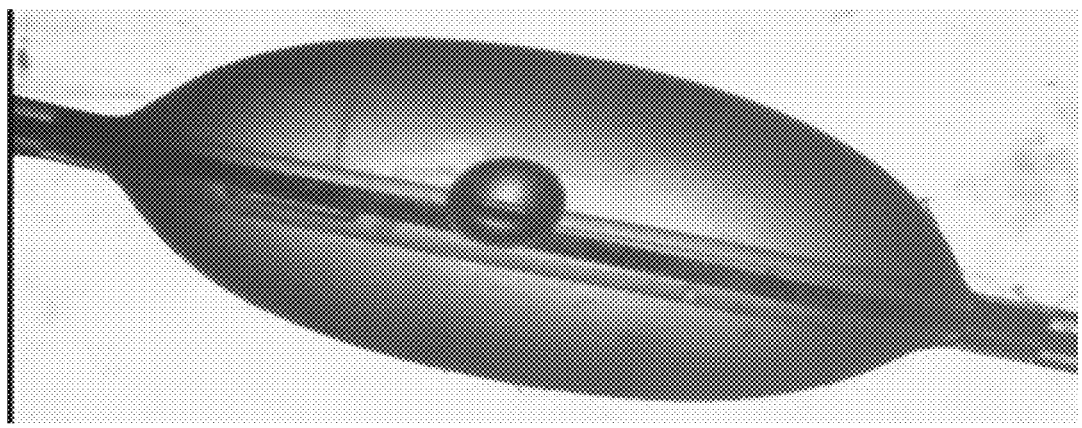
FIG. 11B is a photograph showing the balloon tubing of FIG. 11A inflated to 500%.

FIG. 10 is a photograph showing a post-inflation surface region of the balloon tubing coated with the base coat. As seen in FIG. 10, no cracking was observed on the surface, except for some hairline patterns. FIG. 11A is a photograph showing an uninflated balloon tubing coated with the base coat and the top coat. The tubing had an initial pre-inflation diameter of 1 mm (outer diameter). FIG. 11B is a photograph showing the balloon tubing of FIG. 11A inflated to 500%, i.e., a diameter of about 6 mm. As seen in FIG. 11B, no cracking was observed on the surface.

Figure 11C:
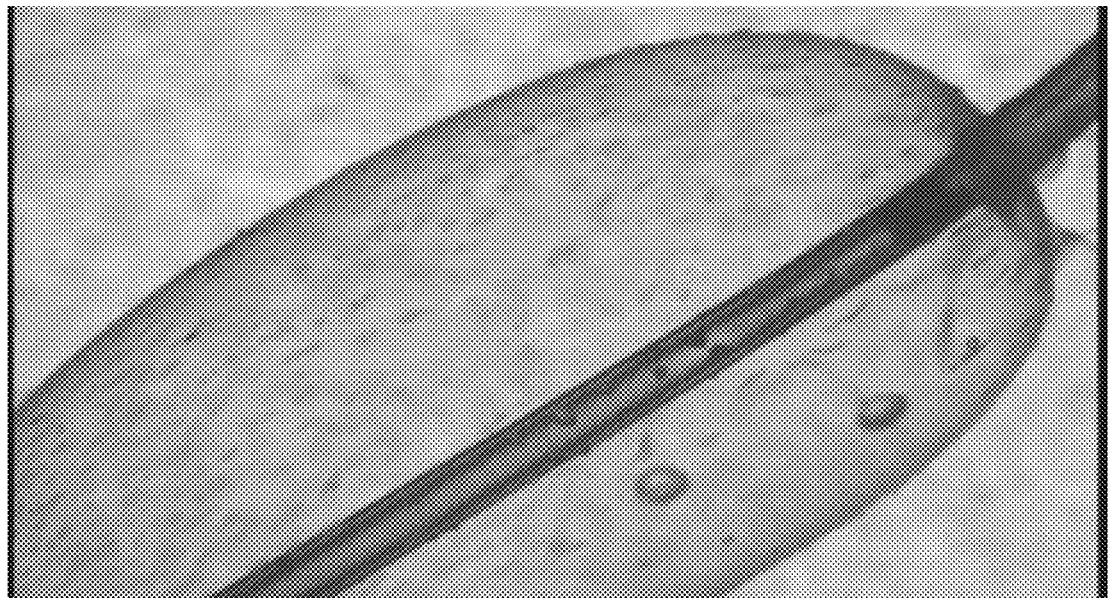
FIG. 11C is a photograph showing the balloon tubing of FIG. 11A inflated to 700%.
Figure 11D:
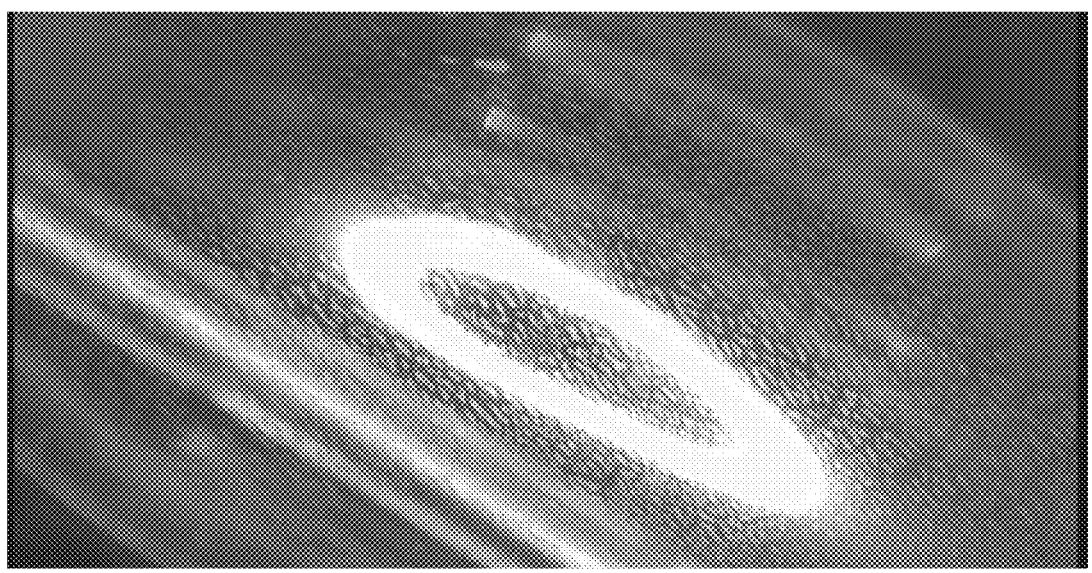
FIG. 11D is a photograph showing a surface region of the balloon tubing of FIG. 11A inflated to 700%.

FIG. 11C is a photograph showing the balloon tubing of FIG. 11A inflated to 700%, i.e., a diameter of about 8 mm. FIG. 11D is a photograph showing a surface region of the balloon tubing of FIG. 11A inflated to 700%. As seen in FIGS. 11C and 11D, some cracking was observed, with no peeling or flaking.

Various examples have been described. These and other examples are within the scope of the following claims.

What is claimed is:

1. A medical device comprising:
    a flexible substrate defining a major surface; and
    a compliant hydrophilic coating at least partially covering the major surface, wherein the compliant hydrophilic coating comprises a base coat and a lubricious top coat, wherein the base coat comprises a copolymer of a thermoplastic elastomer and ethyl acrylate,
    wherein the compliant hydrophilic coating exhibits substantially no cracking or flaking in response to an expansion of the flexible substrate to 500% of an original size of the flexible substrate.

2. The medical device of claim 1, wherein the base coat further comprises at least one of polyethylene oxide or N-vinyl pyrrolidone, and wherein the thermoplastic elastomer comprises at least one of a styrene-isoprene thermoplastic elastomer or a polyolefin elastomer.

3. The medical device of claim 1, wherein the lubricious top coat comprises sodium hyaluronate and azaridine, or comprises a polymer selected from the group consisting of polyvinylpyrrolidone, polyethylene oxide, polypropylene oxide, polyacrylamide, methyl cellulose, polyacrylic acids, polyvinyl alcohols and combinations thereof.

4. The medical device of claim 1, wherein the base coat is a product of thermal curing of a base coat precursor comprising a solvent, wherein the base coat precursor comprises, per 100 weight units of the solvent, about 2 weight units of ethyl acrylate, about 2 weight units of a styrene-isoprene thermoplastic elastomer, and about 1 weight unit of polyethylene oxide.

5. The medical device of claim 1, wherein the base coat is a product of thermal curing of a base coat precursor comprising a solvent, wherein the base coat precursor comprises, per 100 weight units of the solvent, about 2 weight units of ethyl acrylate, about 2 weight units of a styrene-isoprene thermoplastic elastomer, about 2 weight units of a polyolefin elastomer, and about 1 weight unit of N-vinyl pyrrolidone.

6. The medical device of claim 1, wherein the lubricious top coat is a product of thermal curing of a top coat precursor comprising water, wherein the top coat precursor comprises, per 100 weight units of water, between about 0.4 and about 40 weight units of sodium hyaluronate, between about 0.02 and 0.2 weight units of aziridine, and between 0.02 and 0.1 weight units of a surfactant.

7. The medical device of claim 1, wherein the base coat is a product of ultraviolet (UV) curing of a base coat precursor comprising a solvent, wherein the base coat precursor comprises, per 100 weight units of the solvent, about 1.5 weight units of ethyl acrylate, about 1.5 weight units of a polyolefin elastomer, about 1 weight unit of N-vinyl pyrrolidone, and about 0.1 weight units of a UV photoinitiator.

8. The medical device of claim 7, wherein the lubricious top coat is a product of UV curing of a top coat precursor comprising water, wherein the top coat precursor comprises, per 100 weight units of water, between about 0.2 and about 20 weight units of sodium hyaluronate, about 0.5 weight units of aziridine, about 10 weight units of polyvinyl methyl ether maleic anhydride, and between about 0.01 and about 0.05 weight units of the UV photoinitiator.

9. The medical device of claim 1, wherein the base coat is a product of thermal curing of a base coat precursor comprising propylene glycol methyl ether acetate (PGMEA) as solvent, wherein the base coat precursor comprises, per 95 weight units of PGMEA, about 2 weight units of a 2% weight/volume solution of a styrene-isoprene thermoplastic elastomer ethyl acrylate in acetone, about 2 weight units of ethyl acrylate, and about 1 weight unit of 900 Dalton polyethylene oxide dissolved in methanol, and wherein the top coat is a product of thermal curing of a top coat precursor comprising water as solvent, wherein the top coat precursor comprises, per 100 weight units of water, about 2 weight units of sodium hyaluronate, about 0.05 weight units of aziridine, about 0.05 weight units of a surfactant, and about 2 weight units of 900 Dalton polyethylene oxide dissolved in methanol.

10. The medical device of claim 1, wherein the medical device comprises a balloon comprising the flexible substrate.

11. The medical device of claim 1, wherein the medical device comprises an elongated member comprising the flexible substrate.

12. A method comprising:
    applying a base coat precursor comprising a copolymer of a thermoplastic elastomer and ethyl acrylate, and a solvent on a major surface defined by a flexible substrate of a medical device;
    applying a top coat precursor on the base coat precursor; and
    curing the base coat precursor and the top coat precursor to form a compliant hydrophilic coating including a base coat at least partially covering the substrate and a lubricious top coat on the base coat,
    wherein the compliant hydrophilic coating exhibits substantially no cracking or flaking in response to an expansion of the flexible substrate to 500% of an original size of the flexible substrate.

13. The method of claim 12, wherein the curing comprises thermal curing at least one of the base coat precursor and the lubricious top coat precursor.

14. The method of claim 12, wherein the base coat precursor further comprises at least one of polyethylene oxide or N-vinyl pyrrolidone, and wherein the thermoplastic elastomer comprises at least one of a styrene-isoprene thermoplastic elastomer or a polyolefin elastomer.

15. The method of claim 12, wherein the top coat precursor comprises sodium hyaluronate and azaridine, or comprises a polymer selected from a group consisting of polyvinylpyrrolidone, polyethylene oxide, polypropylene oxide, polyacrylamide, methyl cellulose, polyacrylic acids, polyvinyl alcohols, and combinations thereof.

16. The method of claim 12, wherein curing the base coat precursor comprises thermal curing, and wherein the base coat precursor comprises a solvent, and per 100 weight units of the solvent, about 2 weight units of ethyl acrylate, about 2 weight units of a styrene-isoprene thermoplastic elastomer, and about 1 weight unit of polyethylene oxide.

17. The method of claim 12, wherein curing the base coat precursor comprises thermal curing, and wherein the base coat precursor comprises a solvent, and per 100 weight units of the solvent, about 2 weight units of ethyl acrylate, about 2 weight units of a styrene-isoprene thermoplastic elastomer, about 2 weight units of a polyolefin elastomer, and about 1 weight unit of N-vinyl pyrrolidone.

18. The method of claim 12, wherein curing the top coat precursor comprises thermal curing, and wherein the top coat precursor comprises water, and wherein the top coat precursor comprises, per 100 weight units of water, between about 0.4 and about 40 weight units of sodium hyaluronate, between about 0.02 and 0.2 weight units of aziridine, and between 0.02 and 0.1 weight units of a surfactant.

19. The method of claim 12, wherein curing the base coat precursor comprises ultraviolet (UV) curing, and wherein the base coat precursor comprises a solvent, and per 100 weight units of the solvent, about 1.5 weight units of ethyl acrylate, about 1.5 weight units of a polyolefin elastomer, about 1 weight unit of N-vinyl pyrrolidone, and about 0.1 weight units of a UV photoinitiator.

\* \* \* \* \*